United States Patent [19]
Osumi et al.

[11] Patent Number: 6,083,927
[45] Date of Patent: Jul. 4, 2000

[54] HEPATIC DISTURBANCE IMPROVER

[75] Inventors: Yukihiro Osumi, Chiba-ken; Kazuhito Moriya; Tadashi Sasazuka, both of Hokkaido, all of Japan

[73] Assignees: Shirako Co., Ltd.; Hokkaido Sugar Co., Ltd., both of Tokyo, Japan

[21] Appl. No.: 09/307,851

[22] Filed: May 10, 1999

[30] Foreign Application Priority Data

Jun. 9, 1998 [JP] Japan .................................. 10-160526

[51] Int. Cl.$^7$ ...................................................... A01N 43/04
[52] U.S. Cl. ................................. 514/53; 514/54; 514/61; 514/25; 514/893; 536/123.03
[58] Field of Search ................................. 514/53, 54, 61, 514/25, 893; 536/123.03

[56] References Cited

U.S. PATENT DOCUMENTS 5,063,210  11/1991  Lange et al. .............................. 514/54
5,160,736  11/1992  Kiriyama et al. ....................... 424/195

FOREIGN PATENT DOCUMENTS 7-16092  1/1995  Japan .
9-301987  11/1997  Japan .

OTHER PUBLICATIONS

Harrison's Principles of Internal Medicine, McGraw–Hill Inc., 13th edition, chapter 270, p. 1498, 1994.

Yukihiro Osumi et al, "Purification and Characterization of Porphyran–Decomposing Enzymes from *Arthrobacter sp. S–22*," Nippon Suisan Gakkaishi 63(5), 757–764(1997) (with English abstract).

Yukihiro Osumi et al, "Isolation and Identification of a Porphyran–Decomposing Bacterium," Nippon Suisan Gakkaishi 63(4), 709–714 (1997) (with English Abstract).

Yukihiro Osui et al, "Purification and Structure of Oligosaccharides from Porphyran degraded by Enzymes from *Arthrobacter sp. S–22*, " Nippon Suisan Gakkaishi 64(1), 88–97 (1998) (with English Abstract).

Yukihiro Osumi et al, "Effect of Oligosaccharides from Porphyan o In Vitro Digestions, Utilizations by Various Intestinal Bacteria, and Levels of Serum Lipid in Mice," Nippon Suisan Gakkaishi 64(1), 98–104–(1998) (with English Abstract).

*Primary Examiner*—Frederick Krass
*Assistant Examiner*—Donna A. Jagoe
*Attorney, Agent, or Firm*—Oblon, Spivak, McClelland, Maier & Neustadt, P.C.

[57] ABSTRACT

A hepatic disturbance improver which reduces fat in hepatocytes which includes an oligosaccharide of formula (1), (2) or (3), obtainable by hydrolyzing porphyran contained in seaweed of the genus Porphyra. The hepatic disturbance improver is advantageous, in that it reduces fat in hepatocytes without causing side effects.

18 Claims, 1 Drawing Sheet

HEPATIC DISTURBANCE IMPROVER

BACKGROUND OF THE INVENTION

1. Field of the Invention

The present invention relates to a novel hepatic disturbance improver with a strong effect of improving hepatic disturbances.

2. Description of the Related Art

Fatty liver is a lipid metabolism abnormality in hepatocytes in which fat appears and is deposited in an abnormally large amount. It is known that fatty liver in humans is caused by excess nutritional intake such as excessive calorie intake from foods, or may be associated with menopausal disorders, oxygen deficiency, abrupt hyperlipemia, and ulcerous colitis. In normal hepatocytes, the majority of fat is present as lipoprotein and therefore fat deposits do not occur. Fatty liver progresses to hepatocirrhosis over a period of 10 years or more, and thus treatment at an early stage is important. Improvements in everyday habits, such as, reduction of sugar in foods, intake of high-protein foods and suitable exercise, are recommended.

However, mere improvement in everyday habits does not rapidly provide effects, and dietary management restriction for a prolonged period of time cannot be continued in many cases. Further, it is known that fatty liver accompanying hyperlipemia is hardly improved by hyperlipemia-treating agent such as Mevalotin®. Moreover, even administration of polyene phosphatidylcholine as an agent for treating fatty liver is accompanied by problems, in that its relieving effects are weak, long-term administration is necessary, and no sufficient treatment effects have been achieved.

Therefore, in view of the afore-mentioned deficiencies in prior art treatment of fatty liver, it is clear that there still exists in the art a need for such treatments.

SUMMARY OF THE INVENTION

Accordingly, the present invention incorporates a new use of oligosaccharides to obviate the problems associated with conventional methods of improving fatty liver.

An object of the invention is therefore to provide a hepatic disturbance improver for reducing fat in hepatocytes.

Another object of the invention is to provide a method for improving a hepatic disturbance.

With the foregoing and other objects, advantages and features of the invention that will become hereinafter apparent, the nature of the invention may be more clearly understood by reference to the following detailed description and to the appended claims.

BRIEF DESCRIPTION OF THE DRAWINGS

A more complete appreciation of the invention and many of the attendant advantages thereof will be readily obtained as the same becomes better understood by reference to the following detailed description when considered with the following drawing wherein.

DETAILED DESCRIPTION

Figure 1:
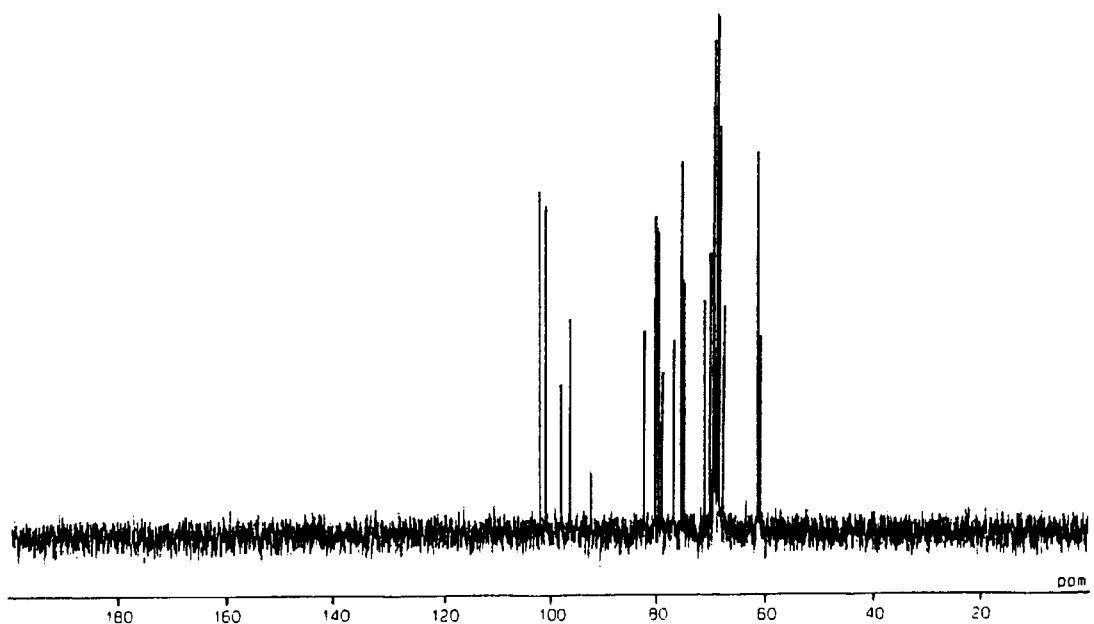
FIG. 1 shows the $^{13}$C-NMR spectrum of formula 3.

The present invention relates to a pharmaceutical preparation containing a galactosulfate oligosaccharide of the following formulas (1) or (2), or a neoagarooligosaccharide of the following formula (3) as an ingredient for reducing fat in hepatocytes, which rapidly improves a hepatic disturbance, for example, fatty liver, at a low dose.

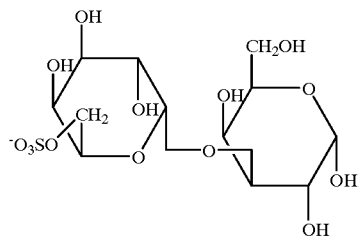

(1)

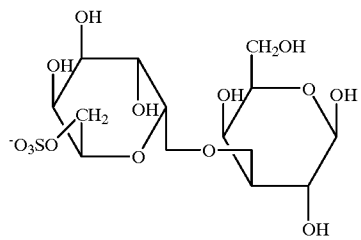

(2)

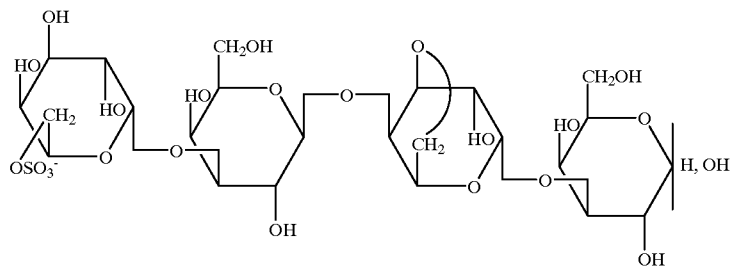

(3)

The galactosulfate oligosaccharide having the formula (1) or (2) used in the present invention is an oligosaccharide obtained by hydrolyzing porphyran contained in seaweeds of the genus Porphyra (Japanese Laid-Open Patent Publication No. 301987/1997 which is incorporated by reference herein in its entirety).

The galactosulfate oligosaccharide (molecular formula, $C_{12}H_{21}O_4S$; molecular weight, 421; structure, 6-sulfategalactopyranosyl-α1,3-(α, β) galactopyranose) is an oligosaccharide developed by the present inventors and obtained by a process in which seaweed of the genus Porphyra including porphyran is hydrolyzed by a microorganism such as S-22 (FERM P-15496) belonging to the genus Arthrobacter having the ability to decompose porphyran contained in seaweeds of the genus Porphyra as a polysaccharide, followed by removal of impurities such proteins to give the oligosaccharide.

The microbial properties of strain S-22 belonging to the genus Arthrobacter, used for producing the galactosulfate oligosaccharide in the present invention, are as follows:

(a) Morphological features
  (1) Cell form and size
    Bacillus with 0.8 μm in width and 0.6 to 4 μm in length.
  (2) Cell polymorphism: the cell length is reduced with an increasing culture time.
  (3) Motility and flagellum adhesion: no motility, no flagellum
  (4) Spore: absent
  (5) Gram stainability: positive
  (6) Acid resistance: absent
(b) Growth states in medium
  (1) Broth agar plate culture
    Size: diameter, 1 to 2.5 mm
    Growth state: moderate
    Protuberance: a rise
    Shape: circular
    Peripheral shape: normal
    Surface state: smooth
    Color: milky-white
    Luster: present
    Property: not viscous
  (2) Bouillon slant culture
    Shape: filamentous
    Growth: moderate
    Protuberance: a rise
    Smell: none
    Surface state: smooth
  (3) Bouillon liquid culture
    Growth on the surface: none
    Fairy-ring formation: none
    Turbidity: slightly turbid in 2-day culture
    Gas formation: none
    Change of indicator color: neutral (greenish blue with BTB)
    Smell: none
  (4) Bouillon gelatin stab culture
    Growth state: Grown 7 mm upwards
    Gelatin liquefaction: none
  (5) Litmus milk medium
    Reaction: none
    Coagulation: present
(c) Physiological properties
  (1) nitrate reduction: none
  (2) denitrification: none
  (3) MR test: negative
  (4) VP test: negative
  (5) indole formation: none
  (6) hydrogen sulfide formation: none
  (7) starch hydrolysis: none
  (8) citric acid utilization: present
  (9) utilization of inorganic nitrogen sources (nitrate): present
    (ammonium salt): present
  (10) pigment formation: none
  (11) urease: positive
  (12) oxidase: negative
  (13) catalase: positive
  (14) growth range (pH): growing at pH 4.5 to 7.5 and not growing at pH 4 (temperature): not growing at 35° C. or more
  (15) attitude toward oxygen: aerobic
  (16) O-F test: no decomposition
  (17) formation of acids and gases from sugars
    (L-arabinose): none
    (D-xylose): none
    (D-glucose): none
    (D-mannose): none
    (D-fructose): none
    (D-galactose): none
    (maltose): none
    (sucrose): none
    (lactose): none
    (trehalose): none
    (D-sorbitol): none
    (inositol): none
    (glycerin): none
    (starch): none
(d) Features showing features of new species
  (1) Decomposed product of sugar: forming a galactosulfate oligosaccharide (6-sulfategalactopyranosyl-α1,3-(α, β) galactopyranose) from porphyran
  (2) Elongation of peripheral cells in a population: present
  (3) Aerial hypha: none
  (4) Diamino acid in cell wall: A3 α, L-Lys-L-Ala-L-Thr-L-Ala
  (5) Glycosyl test: negative (acetyl form)
  (6) Arabinogalactan polymer in cell wall: none
  (7) Quinone system: MK-9 ($H_2$)
  (8) G+C content of microbial DNA: 67 mol % (high performance liquid chromatography)

A method of producing the galactosulfate oligosaccharide using the above strain is also described.

The microorganism is inoculated into a liquid medium containing a powder or a hot-water extract of seaweed of the genus Porphyra, a carbon source such as lactose and galactose, a nitrogen source such as peptone and sodium nitrate, and inorganic salts such as magnesium salts and calcium salts and then cultured at 20 to 30° C., pH 4 to 8, for 2 to 5 days under aerobic conditions, and the cultured broth is sterilized by heating, then filtered or centrifuged to remove the microorganism or precipitates therefrom, followed by precipitation with organic solvent, salting-out, concentration under reduced pressure, absorption and desorption on ion exchanger and activated carbon columns to purify the galactosulfate oligosaccharide.

A neoagaro-oligosaccharide having the formula (3) is also described. This neoagarooligosaccharide is also obtained by hydrolyzing porphyran contained in seaweeds of the genus Porphyra, (Japanese Laid-Open Patent Publication No. 16092/1995 which is incorporated by reference herein in its entirety).

The neoagaro-oligosaccharide composed of 4 sugars is obtained by hydrolyzing porphyran. That is, a microorganism belonging to the genus Pseudomonas having the ability to decompose porphyran, for example Pseudomonas B2411 (FERM P-13637), is cultured in the medium containing porphyran and porphyran-decomposing enzyme is extracted from the above decompositions. The neoagaro-oligosaccharide is obtained by hydrolyzing porphyran contained in seaweeds of the genus Porphyra by using this enzyme.

The properties of Pseudomonas B-2411 are as follows.

(a) Morphological features
  (1) Cell form and size
    Bacillus with 0.5 to 0.8 μm in width and 0.8 to 3 μm in length.
  (2) Cell polymorphism: the flagellum is easily lost.
  (3) Motility and flagellum adhesion: no motility and polar flagellum
  (4) Spore: absent
  (5) Gram stainability: negative
  (6) Acid resistance: absent
(b) Growth conditions in mediums
  (1) Bouillon agar plate culture
    Size: diameter, 4 to 4.5 mm
    Growth state: moderate
    Protuberance: a rise
    Shape: circular or elliptical
    Peripheral shape: normal
    Surface state: smooth
    Color: milky-white
    Luster: present
    Property: viscous
  (2) Bouillon agar slant culture
    Shape: filamentous
    Growth: moderate
    Protuberance: a rise
    Smell: none
    Surface state: smooth
  (3) Bouillon liquid culture
    Growth on the surface: present
    Fairy-ring formation: present
    Turbidity: slightly turbid in 2-day culture
    Gas formation: none
    Change of indicator color: neutral (greenish blue with BTB)
    Smell: none
  (4) Bouillon gelatin stab culture
    Growth state: Grown 5 mm upwards only and present in the form of pill in the medium
    Gelatin liquefaction: none
  (5) Litmus milk medium
    Reaction: none (bluish violet)
    Coagulation: present
(c) Physiological properties
  (1) nitrate reduction: none
  (2) denitrification: none
  (3) MR test: negative
  (4) VP test: negative
  (5) indole formation: none
  (6) hydrogen sulfide formation: none
  (7) starch hydrolysis: none
  (8) citric acid utilization: none
  (9) utilization of inorganic nitrogen sources (nitrate): present
    (ammonium salt): present
  (10) pigment formation: none
  (11) urease: negative
  (12) oxidase: negative
  (13) catalase: positive
  (14) growth range (pH): growing at pH 4.5 to 7.5 and not growing at pH 4
    (temperature): not growing at 35° C. or more
  (15) attitude toward oxygen: aerobic
  (16) O-F test: no decomposition
  (17) formation of acids and gases from sugars
    L-arabinose: none
    D-xylose: none
    D-glucose: none
    D-mannose: none
    D-fructose: none
    D-galactose: none
    maltose: none
    sucrose: none
    lactose: none
    trehalose: none
    D-sorbitol: none
    inositol: none
    glycerin: none
    starch: none
(d) Features showing features of new species
  (1) Decomposed product of sugar: forming an oligosaccharide based di- and tetra-oligosaccharides from porphyran
  (2) Arginine decomposition: none
  (3) Temperature resistance: perished at 85° C. for 10 minutes or at 80° C. for 30 minutes
  (4) Resistance to sodium chloride: growing at 0 to 3% (in peptone water)
  (5) Lipase: Decomposing Tween 80 (in 1% Tween-peptone water)
  (6) G+C content of microbial DNA: 62.7 mol % (high performance liquid chromatography)

For production of an enzyme which forms the neoagaro-oligosaccharide from the above strain, the strain is cultured in a medium.

Either liquid or solid medium may be used for culturing the strain. Usually, a method using a liquid medium is preferable. Culture under aeration and agitation is industrially preferable. The medium should contain a carbon source and a nitrogen source utilizable by the strain, as well as various ingredients necessary for growth of the strain and for formation of the enzyme.

As the carbon source, starch, dextrin, sucrose, lactose, maltose, glucose, galactose, fructose, black strap molasses and the like can be used for growth of the strain, and crude porphyran-containing materials or porphyran should be added for formation of the enzyme. As the nitrogen source, inorganic or organic nitrogenous materials such as ammonium salts, nitrates, corn steep liquor, peptone, meat extract, casamino acid, soybean powder, wheat bran, urea etc. are used. In addition, yeast extract and dried yeast are effective for increasing the amount of enzyme produced. As the inorganic salts, magnesium salts, calcium salts, sodium salts, phosphates, iron salts, manganese salts, zinc salts etc. are used, and in particular magnesium salts are important.

Further, nutrients such as vitamins, growth promoters etc. may be added as necessary.

A preferable medium composition is, for example, a combination of peptone, yeast extract, galactose, porphyran, dipotassium hydrogen phosphate, sodium chloride, magnesium sulfate and calcium chloride.

The culture temperature is preferably about 20 to 30° C. and the culture pH is preferably from 4 to 8. The microorganism is cultured under aerobic conditions for 2 to 5 days. Because the above enzyme is produced in the broth after culturing, the microorganism is removed from the cultured broth by filtration or centrifugation and the enzyme solution is thereby obtained. The enzyme solution is subjected to conventional enzyme purification methods such as precipitation with an organic solvent, salting-out, concentration under reduced pressure, absorption and desorption on ion exchangers and gel fractionation, whereby the enzyme is purified.

This enzyme acts specifically on porphyran which is a component in seaweed of the genus Porphyra, to form the neoagaro-oligosaccharide.

This crude neoagaro-oligosaccharide was purified again by a Sephadex G-10 column, and the molecular weight of the purified oligosaccharide, as determined by a mass spectrometer (SIMS-MS) with glycerol as matrix, was 727. It was analyzed by nuclear magnetic resonance ($^{13}$CNMR). A chemical shift at 58.8 ppm assigned to a methyl group did not occur, so it showed a NMR spectrum similar to that of 6-0-methylgalactose-free monosulfated tetrasaccharide out of oligosaccharides obtained by allowing agarase derived from *Pseudomonas atlantica* to act on porphyran. The $^{13}$C-NMR spectrum of this purified neoagarooligosaccharide is shown in FIG. 1. From the foregoing, the neoagarooligosaccharide used in the present invention has the following formula:

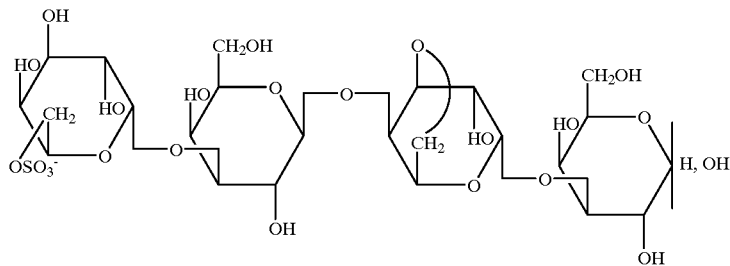

(3)

The properties of the above enzyme are shown in Table 1.

TABLE 1

| Properties of the purified enzyme | | |
|---|---|---|
| | CM-IIbaa fraction | CM-IIIdaa fraction |
| Molecular weight | 28,000 | 42,000 |
| Isoelectric point | 5.2 | 6.8 |
| Optimum pH* | 6 | 5 |
| Optimum temperature (° C.)* (reaction for 20 minutes) | 60 | 50 |
| Stable pH* (37° C., 1 hour) | 6 to 8 | 5 to 9.5 |
| Thermostability* | residual activity 95% (40° C.) (pH 6.1, 1 hour) | residual activity 95% (45° C.) (pH 5, 1 hour) |
| Effects of metals* | | |
| Activation | Fe2+ | Fe2+ |
| Inhibition | Cu2+, Zn2+, Hg2+ Al3+, Mn2+ | Cu2+, Zn2+, Hg2+ Al3+, Mn2+ |
| Substrate specificity* | porphyran | porphyran |
| Hydrolyzing | κ-carrageenan | κ-carrageenan |
| Not hydrolyzing | lactose pectin dextran agar | lactose pectin dextran agar |

*Enzyme activity was measured by reducing sugars liberated.

The enzyme was added to a crude porphyran solution containing a small amount of toluene, followed by incubation at 37° C. for 48 hours, and then a supernatant obtained by removing insolubles or polymeric materials by centrifugation and precipitate by successive addition of ethylalcohol was concentrated. It was then applied to an ion-exchange column Super Q-Toyopearl 650 M and the absorbed fraction was eluted with sodium chloride-containing water as eluent and then fractionated and desalted through a Sephadex G-10 column whereby crude 60% neoagaro-oligosaccharide of the structural formula (3) was obtained.

Any of the above oligosaccharides reduce accumulation of fat in hepatocytes to improve the effect of improving hepatic disturbances. If these oligosaccharides are taken as the hepatic disturbance improver of the present invention, it is used preferably in the range of 3 to 10 mg/kg/day, and if it is used as a dose more than 10 mg/kg/day, its pharmaceutical manufacturing suitability may be deteriorated. Further, any of the oligosaccharides when used as the hepatic disturbance improver may be purified or in a crude form.

The oligosaccharides of the hepatic disturbance improver of the present invention can be formed into arbitrary forms such as tablets, capsules, powder etc. For pharmaceutical manufacturing, other additives such as stabilizers, fillers, weighting agents etc. can be added to the oligosaccharides of the present invention.

EXAMPLES

Hereinafter, the present invention is described in more detail with reference to Examples, which however is not intended to limit the scope of the present invention.

Example 1

A crude galactosulfate oligosaccharide (containing about 42% disaccharide) and a purified galactosulfate oligosaccharide (containing about 96% disaccharide) were produced by the following method.

20 ml of a liquid medium consisting of 0.5% porphyran, 0.42% peptone, 0.01% yeast extract, 0.1% sodium chloride, 0.25% magnesium sulfate.7H$_2$O and 0.01% calcium chloride.2H$_2$O was adjusted to pH 7, then introduced to a 100-ml Erlenmeyer flask, and sterilized at 121° C. Strain S-22 was inoculated into this medium and cultured at 25° C. for 4 days with stirring (200 r.p.m.).

Then, 15 L liquid medium consisting of 4% seaweed powder (dry seaweed was ground and passed through a 0.25 mm screen), 0.1% peptone, 0.05% yeast extract, 0.01% sodium chloride, 0.25% magnesium sulfate.7H$_2$O and 0.01% calcium chloride.2H$_2$O was adjusted to pH 6, then introduced to a 30-L jar fermenter and steam-sterilized. 150 ml of the previous culture was inoculated into it and cultured at 28° C. at 400 r.p.m. at an aeration rate of 15 L/min. for 60 hours while the culture was adjusted to pH 7.5 with 10% hydrochloric acid. The culture was filtered with a filter assist (Celite), then concentrated to 800 ml through Saltcom Module membrane (cut off molecular weight 10,000), precipitated between 30 and 70% saturation with ammonium sulfate, dialyzed in a cellulose dialysis membrane, and concentrated as a crude enzyme.

Separately, 15 g of crude porphyran was added to 500 ml of 10 mM acetate buffer, pH 5.5 containing a small amount of toluene, and it was dissolved under pressure by heating at 121° C. for 20 minutes. After it was gradually cooled, 75 U of the crude enzyme obtained above was added thereto and reacted at 37° C. for 48 hours.

After reaction, insoluble materials were removed by centrifugation (20,000× g, 20 minutes) and ethanol was added thereto at a final concentration of 70% to remove polymeric materials.

300 ml of the supernatant was concentrated to 43 ml by an evaporator and lyophilized to give 2.5 g dried crude galactosulfate oligosaccharide to be used in accordance with the present invention.

This crude galactosulfate oligosaccharide was analyzed using combined columns (Shodex OH pak KS-804 and lonpak KS-802) with 5 mM sodium chloride as eluent, indicating that it was composed of the galactosulfate oligosaccharide (56%) at a retention time of 19.931 minutes and the neoagaro-oligosaccharide (7.9%) at a retention time of 18.86 minutes.

Further, the effect of improving various cholesterol levels in the liver by administration of the crude galactosulfate oligosaccharide was examined. 4-week-old ICR type male mice bred with feed supplemented with cholesterol and colic acid (as a result, mice loaded with cholesterol and colic acid) were divided into 4 groups (8 mice/group), that is, a 0.2% galactosulfate oligosaccharide administration group, a 0.6% galactosulfate oligosaccharide administration group, a 0.03% Mevalotin (r) (i.e., treatment agent for hyperlipemia, Sankyo Co., Ltd.) administration group, and a non-administration group (control group). Furthermore, a group given standard feed (Oriental Yeast Co., Ltd.) comprising 8 mice was prepared. These 5 groups were bred further for 28 days and then starved, and their livers were excised and perfused with physiological saline, and the same amount of these samples were weighed and collected, and the values shown in Table 2 were measured by an enzymatic method. The results are shown in Table 2.

TABLE 2

Change in hepatic cholesterol by administration of galactosulfate oligosaccharide and Mevalotin ®

| Group | Total cholesterol | neutral fat | phospholipid |
|---|---|---|---|
| Galactosulfate oligosaccharide (0.2%) | 2.0 ± 0.2* | 10.9 ± 1.0* | 13.4 ± 1.4* |
| Galactosulfate oligosaccharide (0.6%) | 1.0 ± 0.1* | 10.3 ± 0.7* | 12.6 ± 1.0* |
| Mevalotin (0.03%) | 3.6 ± 0.3* | 12.9 ± 1.8* | 18.8 ± 0.9* |
| High-fatty-feed control group | 3.0 ± 0.0# | 11.8 ± 1.3# | 15.2 ± 0.6# |
| Standard-feed control group | 1.9 ± 0.1 | 9.7 ± 1.3 | 13.2 ± 0.6 |

Unit: mg/g, *There is a significance of 5% relative to the high-fatty-feed control group.
There is a significance of 5% relative to the standard-feed group.

As shown in Table 2, when the crude galactose sulfate oligosaccharide of the present invention is administrated, any of the total cholesterol, neutral fat and phospholipid were reduced as compared with the high-fat feed control group and its improvement was similar to that of the standard-feed group. On the other hand, Mevalotin(r) used as a treatment agent for hyperlipemia did not have the effect of reducing hepatic cholesterol, to indicate higher cholesterol levels than the cholesterol control group.

Example 2

A hepatic disturbance improver containing 200 mg of the crude galactosulfate oligosaccharide per capsule, obtained in Example 1, was produced. Eight 45- to 65-year-old adult humans with high γ-GTP levels in blood examination were given 3 capsules/day/person for 90 days and then their bloods were collected and examined for γ-GTP levels by an enzymatic method. During the test, dietary limitation was not done, and only the administration of an anti-cholesterol agent etc. was limited. The results are shown in Table 3.

TABLE 3

Change in γ-GTP levels by administration of the crude galactosulfate oligosaccharide

| | γ-GTP levels before administration | γ-GTP levels after administration |
|---|---|---|
| A (male, 54-year-old) | 75 | 59 |
| B (male, 60-year-old) | 70 | 50 |
| C (male, 57-year-old) | 85 | 68 |
| D (male, 49-year-old) | 73 | 58 |
| E (male, 62-year-old) | 77 | 52 |
| F (male, 45-year-old) | 81 | 63 |
| G (female, 58-year-old) | 69 | 54 |
| H (female, 65-year-old) | 74 | 60 |

Unit: U/L

As shown in Table 3, any of the levels measured after administration were reduced, indicating that the crude galactosulfate oligosaccharide improved the functions of the liver.

Example 3

The neoagaro-oligosaccharide (containing about 70% tetrasaccharide) was produced in the following method.

20 ml of a liquid medium consisting of 0.5% porphyran, 0.42% peptone, 0.01% yeast extract, 0.1% sodium chloride, 0.25% magnesium sulfate.7H$_2$O and 0.01% calcium chloride.2H$_2$O was adjusted to pH 7, then introduced a 100-ml Erlenmeyer flask, and sterilized at 121° C. Strain S-2411 was inoculated into this medium and cultured at 25° C. for 4 days with stirring (200 r.p.m.).

Then, 15 L liquid medium consisting of 4% seaweed powder (dry seaweed was ground and passed through a 0.25 mm screen), 0.1% peptone, 0.05% yeast extract, 0.01% sodium chloride, 0.25% magnesium sulfate.7H$_2$O and 0.01% calcium chloride.2H$_2$O was adjusted to pH 6, then introduced a 30-L jar fermenter, and steam-sterilized. 150 ml of the previous culture was inoculated into it and cultured at 28° C. at 400 r.p.m. at an aeration rate of 15 L/min. for 60 hours while the culture was adjusted to pH 7.5 with 10% hydrochloric acid. The culture was filtered with a filter assist (Celite), then concentrated to 650 ml through a Saltcom Module membrane (cut off molecular weight 10,000), precipitated between 30 and 70% saturation with ammonium sulfate, dialyzed in a cellulose dialysis membrane, and concentrated to a crude enzyme.

Separately, 15 g of crude porphyran was added to 500 ml of 10 mM acetate buffer, pH 5.5 containing a small amount of toluene, and it was autoclaved at 121° C. for 20 minutes. After it was gradually cooled, 90 U of the crude enzyme obtained above was added thereto and reacted at 37° C. for 48 hours.

After reaction, insolubles were removed by centrifugation (20,000× g, 20 minutes) and ethanol was added thereto at a final concentration of 70% to remove polymeric materials.

300 ml of the supernatant was concentrated to 35 ml by an evaporator and lyophilized to give 1.5 g of the dried crude galactosulfate oligosaccharide of the present invention.

This crude galactosulfate oligosaccharide was analyzed using combined columns (Shodex OH pak KS-804 and Ionpak KS-802) with 5 mM sodium chloride as an eluent, indicating that it was composed of the neoagarooligosaccharide (68%) at a retention time of 18.86 minutes and the galactosulfate oligosaccharide (21%) at a retention time of 19.931 minutes.

This sample was used to produce a hepatic disturbance improver containing 200 mg of the neoagarooligosaccharide per capsule. Eight 42- to 63-year-old adult humans with high γ-GTP levels in blood examination were given 3 capsules/day/person for 90 days and then their bloods were collected and examined for γ-GTP levels by an enzymatic method. During the test, the dietary limitation was not done, and only the administration of an anticholesterol agent etc. was limited. The results are shown in Table 4.

TABLE 4

Change in γ-GTP levels by administration of neoagaro-oligosaccharide

| | γ-GTP levels before administration | γ-GTP levels after administration |
|---|---|---|
| I (male, 42-year-old) | 78 | 64 |
| J (male, 54-year-old) | 72 | 63 |
| K (male, 46-year-old) | 75 | 66 |
| L (male, 63-year-old) | 70 | 62 |
| M (female, 56-year-old) | 82 | 64 |
| N (female, 49-year-old) | 80 | 61 |

TABLE 4-continued

Change in γ-GTP levels by administration of neoagaro-oligosaccharide

| | γ-GTP levels before administration | γ-GTP levels after administration |
|---|---|---|
| O (female, 61-year-old) | 75 | 59 |
| P (female, 53-year-old) | 69 | 57 |

Unit: U/L

As shown in Table 4, any of the levels measured after administration were reduced, thus indicating that the neoagaro-oligosaccharide improved the functions of the liver.

As described above, the galactosulfate oligosaccharide and neoagaro-oligosaccharide as the ingredients in the present invention have the effect of reducing fat in hepatocytes. Furthermore, the starting materials of these oligosaccharides are seaweeds of the genus Porphyra, so there is the advantage that there is less worry about side effects. Therefore, according to the present invention, a hepatic disturbance improver which can be administered for a prolonged period of time can be provided.

Japanese application Hei-10-160526, filed Jun. 9, 1998 is incorporated by reference.

What is claimed is:

1. A hepatic disturbance improver containing a galactosulfate oligosaccharide of the following formula:

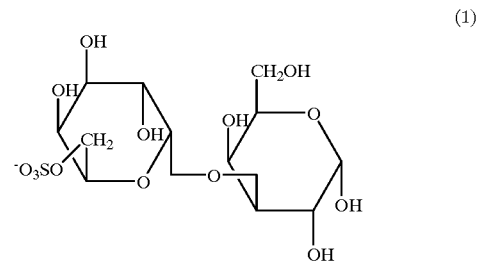

or

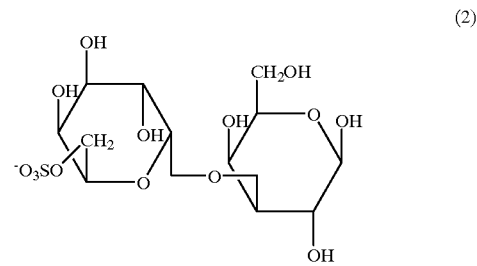

2. A hepatic disturbance improver containing a neoagaro-oligosaccharide of the following formula:

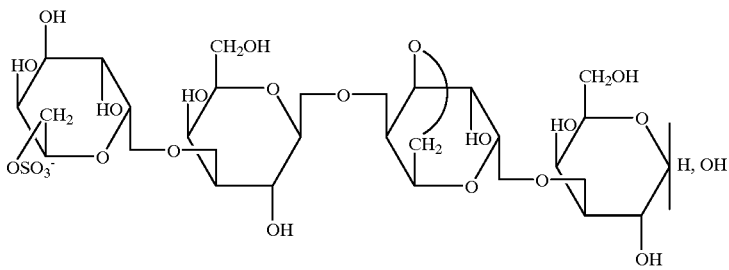

(3)

3. A hepatic disturbance improver according to claim 1 wherein the hepatic disturbance is fatty liver.

4. A hepatic disturbance improver according to claim 2 wherein the hepatic disturbance is fatty liver.

5. A method for improving a hepatic disturbance, comprising administering to a patient in need thereof, an amount of the hepatic disturbance improver of claim 1 sufficient to improve the hepatic disturbance.

6. A method for improving a hepatic disturbance, comprising administering to a patient in need thereof, an amount of the hepatic disturbance improver of claim 2 sufficient to improve the hepatic disturbance.

7. The method of claim 5, wherein said amount is 3–10 mg/kg/day.

8. The method of claim 6, wherein said amount is 3–10 mg/kg/day.

9. The hepatic disturbance improver of claim 1 in the form of a tablet, capsule or powder.

10. The hepatic disturbance improver of claim 2 in the form of a tablet, capsule or powder.

11. The hepatic disturbance improver of claim 9, in the form of a capsule.

12. The hepatic disturbance improver of claim 10, in the form of a capsule.

13. The hepatic disturbance improver of claim 11, wherein said capsule comprises 200 mg neoagarooligosaccharide per capsule.

14. The hepatic disturbance improver of claim 12, wherein said capsule comprises 200 mg neoagarooligosaccharide per capsule.

15. The method of claim 5, wherein the hepatic disturbance improver is in the form of a capsule.

16. The method of claim 6, wherein the hepatic disturbance improver is in the form of a capsule.

17. The method of claim 16, wherein said capsule comprises 200 mg neoagarooligosaccharide per capsule.

18. The method of claim 17, wherein said capsule is administered 3 times per day.

* * * * *